United States Patent [19]
Mathias et al.

[11] Patent Number: 6,132,413
[45] Date of Patent: Oct. 17, 2000

[54] BREAKABLE CANNULA ASSEMBLIES AND METHODS FOR MANIPULATING THEM

[75] Inventors: Jean-Marie Mathias, Lillois; Jean-Claude Bernes, Faimes; Peter Meeremans, Aalter, all of Belgium

[73] Assignee: Baxter International Inc., Deerfield, Ill.

[21] Appl. No.: 09/036,337

[22] Filed: Mar. 6, 1998

[51] Int. Cl.7 ...................................................... A61M 5/00
[52] U.S. Cl. ........................... 604/403; 604/408; 604/415
[58] Field of Search ..................................... 604/403, 408, 604/411, 414, 415, 416, 905, 533

[56] References Cited

U.S. PATENT DOCUMENTS

| | | |
|---|---|---|
| 3,217,710 | 11/1965 | Beall et al. . |
| 3,750,645 | 8/1973 | Bennett et al. . |
| 4,007,738 | 2/1977 | Yoshino . |
| 4,181,140 | 1/1980 | Bayham et al. . |
| 4,195,632 | 4/1980 | Parker et al. . |
| 4,270,534 | 6/1981 | Adams . |
| 4,294,247 | 10/1981 | Carter et al. . |
| 4,340,049 | 7/1982 | Munsch . |
| 4,386,622 | 6/1983 | Munsch . |
| 4,430,049 | 2/1984 | Aiba . |
| 4,479,989 | 10/1984 | Mahal . |
| 4,586,928 | 5/1986 | Barnes et al. . |
| 4,621,634 | 11/1986 | Nowacki et al. ................. 128/204.18 |
| 5,188,629 | 2/1993 | Shimoda . |
| 5,304,163 | 4/1994 | Bonnici et al. . |
| 5,330,464 | 7/1994 | Mathias et al. . |
| 5,514,123 | 5/1996 | Adolf et al. ............................. 604/411 |

FOREIGN PATENT DOCUMENTS

| | | |
|---|---|---|
| 0 177 859 | 10/1984 | European Pat. Off. . |
| 0 330 130 | 2/1989 | European Pat. Off. . |
| 0 455 215 | 4/1991 | European Pat. Off. . |
| 0 462 548 | 6/1991 | European Pat. Off. . |
| 0 555 927 | 2/1993 | European Pat. Off. . |
| 0 803 267 | 4/1997 | European Pat. Off. . |
| 2 716 389 | 2/1994 | France . |
| 32 38 836 | 9/1983 | Germany . |
| 4116474 | 5/1991 | Germany . |
| 572176 | 9/1943 | United Kingdom . |
| 2020253 | 5/1978 | United Kingdom . |
| WO91/11152 | 1/1991 | WIPO . |
| WO 95/08299 | 9/1993 | WIPO . |

*Primary Examiner*—Glenn K. Dawson
*Assistant Examiner*—David J. Cho
*Attorney, Agent, or Firm*—Daniel D. Ryan; Amy L. H. Rockwell; Bradford R. L. Price

[57] ABSTRACT

A breakable seal is located within a housing. The housing includes a ribbed region of restricted diameter protruding from the wall into the bore. A breakable juncture in the seal joins the tip of a cannula member to the base of the cannula member. The leading portion of the tip is free of any projection that frictionally engages either the wall or the ribbed region. Thus, neither the wall nor the ribbed region contacts or constrains movement of the leading portion in the bore when the tip is broken from the base. The trailing portion of the tip carries at least one projection constructed to frictionally engage the ribbed region. The ribbed region constrains movement of the trailing portion through the bore when the tip is broken from the base. By rocking the cannula tip, the juncture can be broken and the cannula tip advanced to a secure position in the housing.

13 Claims, 4 Drawing Sheets

FIG. 4
FIG. 5
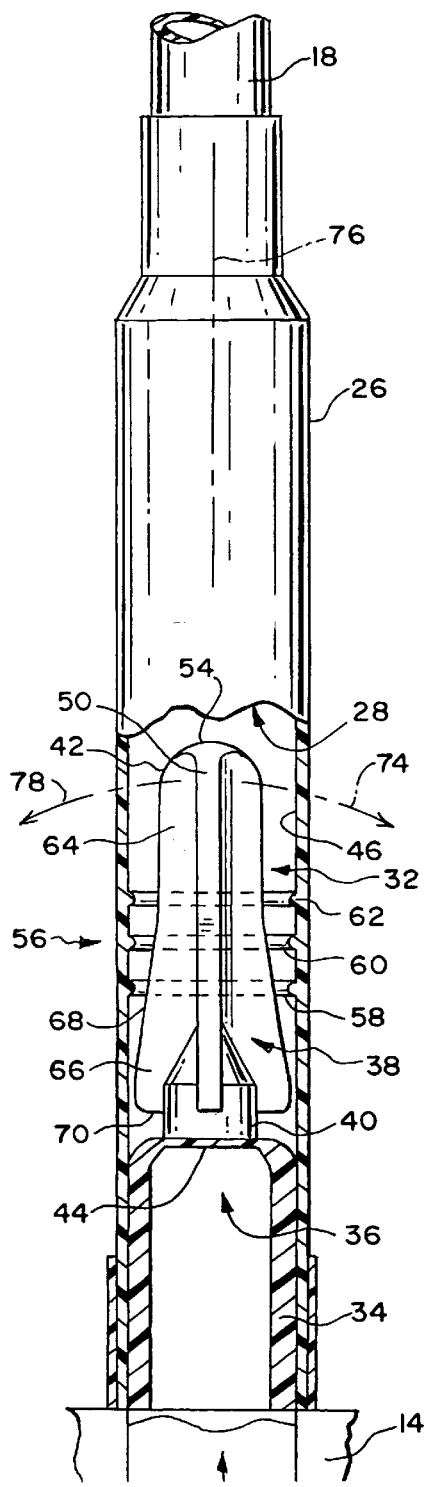
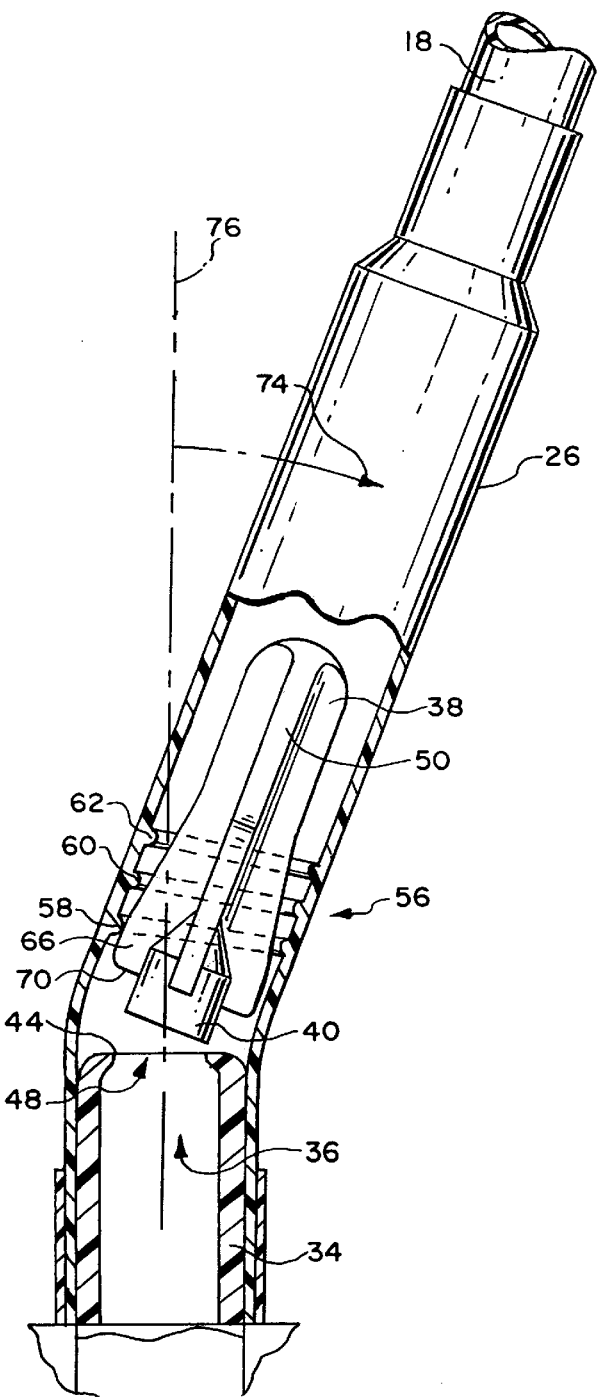

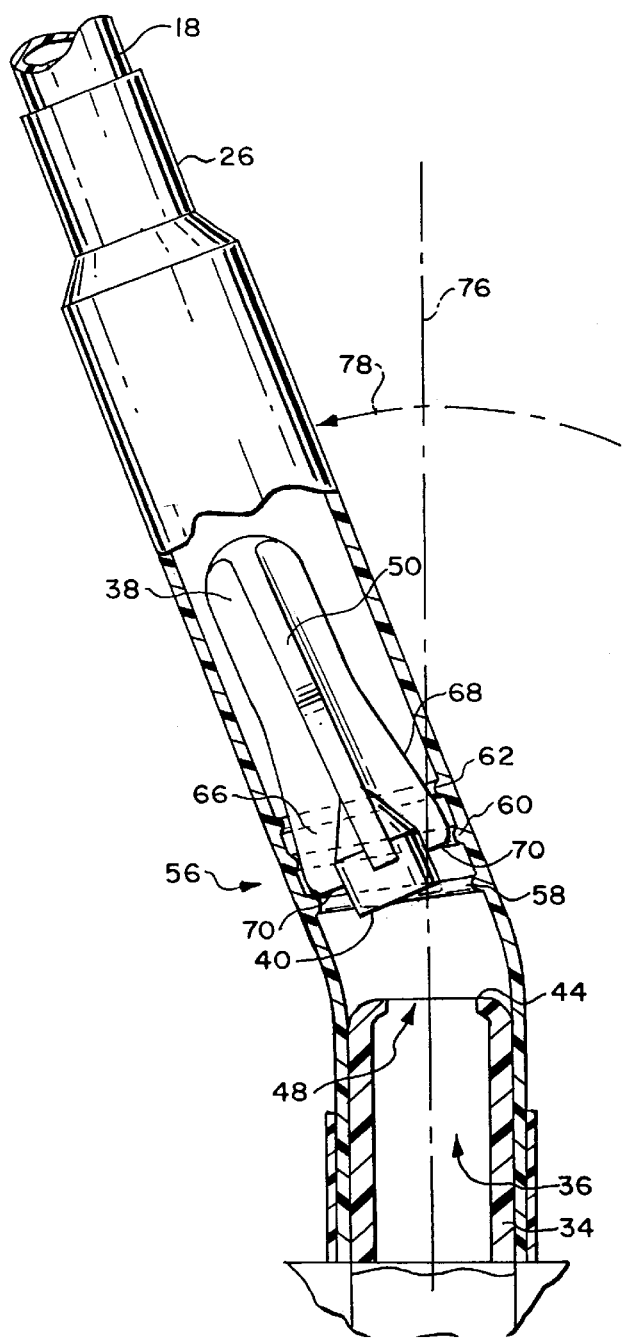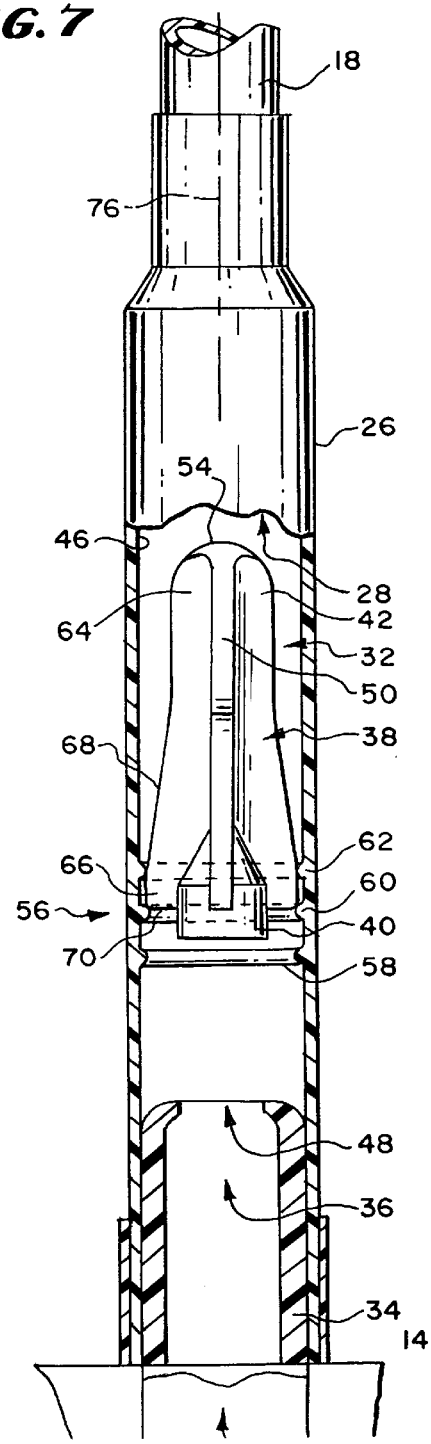

BREAKABLE CANNULA ASSEMBLIES AND METHODS FOR MANIPULATING THEM

FIELD OF THE INVENTION

The invention relates to breakable or frangible seals for fluid paths.

BACKGROUND OF THE INVENTION

Mathias et al. U.S. Pat. No. 5,330,464 discloses a breakable seal located within a fluid path. The seal comprises a rigid, break-apart plastic cannula member, which lays within a flexible plastic housing. Mathias '464 disclose projections on both the front and back ends of the cannula member, which engage the wall of the flexible housing to restrain the cannula member, once broken, from moving inside the housing.

Frangible seals of the type shown in Mathias '464 are widely used in association with multiple blood bag systems. These systems undergo centrifugation during normal use. During centrifugation, the flexible housing, which encloses the cannula member, can bend about the front end of the cannula member. Exposed to centrifugal forces, the projections on the front end of the cannula member can penetrate and even puncture the plastic walls of the housing.

SUMMARY OF THE INVENTION

The invention provides improved breakable seals for fluid paths, as well as improved ways to manipulate breakable seals.

According to one aspect of the invention, the seal includes a break-apart cannula member. The break-apart cannula member is free of any projections on its leading or front portion to frictionally engage the wall of the surrounding flexible housing. Instead, the housing includes a ribbed region of multiple rings placed inside the housing. The ribbed region frictionally engages a projection on the trailing portion of the cannula member. This singular engagement at the trailing portion of the cannula member constrains movement of the cannula member in the bore, when broken to establish fluid communication.

The lack of projections on the leading portion of the cannula member protects the housing wall against unintended point contact with the leading portion of the tip. The singular restraint, which is formed by the frictional contact between the ribbed region and the projection on the trailing portion of the cannula member, is effective to stabilize the position of the cannula member in the housing, when broken to establish fluid communication.

According to another aspect of the invention, a breakable seal includes a resilient housing, which comprises a wall defining a bore having an axis and an interior diameter. The housing also includes a number of rings, spaced apart along the axis, which protrude from the wall into the bore. Each ring has a restricted diameter less than the interior diameter of the wall.

This aspect of the invention provides a cannula assembly in the bore. The cannula assembly comprises a base, a tip, and a breakable juncture between the tip and base. The tip includes a trailing portion, which carries at least one projection extending from different sides of the tip and constructed to frictionally engage the rings.

This structure makes efficient manipulation of the breakable seal possible. For example, in one embodiment, the resilient housing can be bent in a first direction across the axis to deflect the tip and open the breakable juncture, while also advancing one side of the projection past a first one of the rings. The resilient housing can then be bent in a different, second direction across the axis to pivot the one side of the projection against the first ring, while an other side of the projection advances past the first ring. As a result of the rocking action, all sides of the projection are located past the first ring, which resists movement of the cannula tip in its direction along the axis of the housing.

In a preferred embodiment, the resilient housing can be bent in a first direction across the axis to deflect the tip and open the breakable juncture, while also advancing one side of the projection past a first one of the rings. The resilient housing can then be bent in a different, second direction across the axis to pivot the one side of the projection against the first ring, while an other side of the projection advances past the first ring and also past a second one of the rings. The resilient housing can then be returned to alignment with the axis, to pivot the other side of the projection against the second ring while the one side of the projection advances past the second ring. As a result of the rocking action, all sides of the projection are past the second ring, which resists further movement of the cannula tip in its direction along the axis of the housing.

In a preferred embodiment, a third ring is spaced from the second ring at a position along the axis opposite to the first ring. As a result of the rocking action, all sides of the projection are between the second and third rings. The second ring resists movement of the cannula tip in one direction along the axis of the housing, while the third ring resists movement of the cannula housing in the opposite direction.

According to this aspect of the invention, straightforward rocking action both opens the breakable juncture and advances the cannula tip to secure position in the housing.

The features and advantages of the invention will become apparent from the following description, the drawings, and the claims.

BRIEF DESCRIPTION OF THE DRAWINGS

FIG. 4 is a side view of the breakable cannula assembly, with portions broken away, when assembled and before the tip of the cannula member has been broken from the base of the cannula member;

FIG. 5 is a side view of the breakable cannula assembly, with portions broken away, being deflected in one direction to break the cannula tip from the cannula base, as well as advance the cannula tip in a ribbed area away from the cannula base;

FIG. 6 is a side view of the breakable cannula assembly, with portions broken away, being deflected in a different direction than FIG. 5 to further advance the cannula tip in the ribbed area away from the cannula base; and FIG. 7 is a side view of the breakable cannula assembly, with portions broken away, having returned from its deflected condition shown in FIG. 6, and showing the cannula tip lodged in secure, frictional engagement in the ribbed area of the housing, away from the cannula base.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
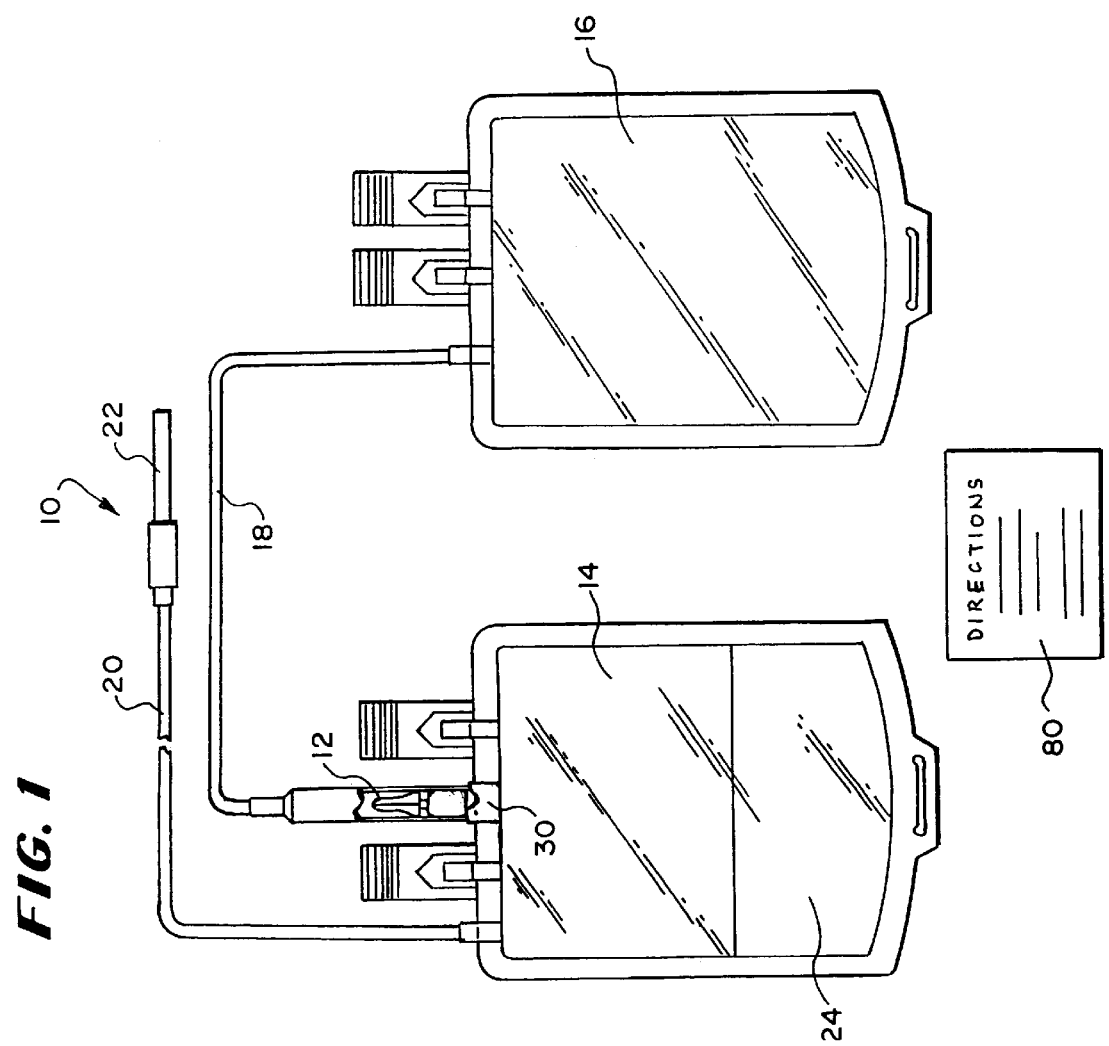
FIG. 1 is a plan view of a multiple blood bag system, which includes a breakable cannula assembly that embodies features of the invention.

FIG. 1 shows a multiple bag system 10, which includes a breakable cannula assembly 12 that embodies the features of the invention. The bag system 10 comprises first and second bags 14 and 16 interconnected by a transfer tube 18. In use, the cannula assembly 12 normally blocks fluid flow through the transfer tube 18. The cannula assembly 12 can be broken open by manual manipulation of the user, to open the transfer tube 18 to fluid flow.

In the illustrated embodiment, the bag system 10 is intended to be used to collect and process blood. Still, it should be appreciated that the cannula assembly 12 is well suited for use with other types of containers or other systems that receive, store, or deliver fluids in the medical field.

In the illustrated embodiment, the first bag 14 is intended to receive whole blood from a donor. For this reason, the first bag 14 includes another integrally attached tube 20, which carries a phlebotomy needle 22. The first bag 14 also contains an anticoagulant solution 24, which mixes with the whole blood conveyed by the tube 20 into the bag 14.

After collecting a desired unit of whole blood, the tube 20 is sealed and parted. The bag system 10 is centrifuged to separate the whole blood in the first bag 14 into components, e.g., red blood cells, plasma, and an intermediate interface containing leukocytes (also called the buffy coat).

After centrifugation, the cannula assembly 12 is broken open. Plasma is expressed from the first bag 14 into the second bag 16 through the transfer tube 18, leaving the red blood cells and buffy coat in the first bag 14. The transfer tube 18 is sealed and parted to allow the contents of the first and second bags 14 and 16 to be further processed or stored separately.

In the illustrated embodiment, the first and second bags 14 and 16 and associated tubes 18 and 20 are made, e.g., from medical grade plasticized polyvinyl chloride material.

Figure 3:
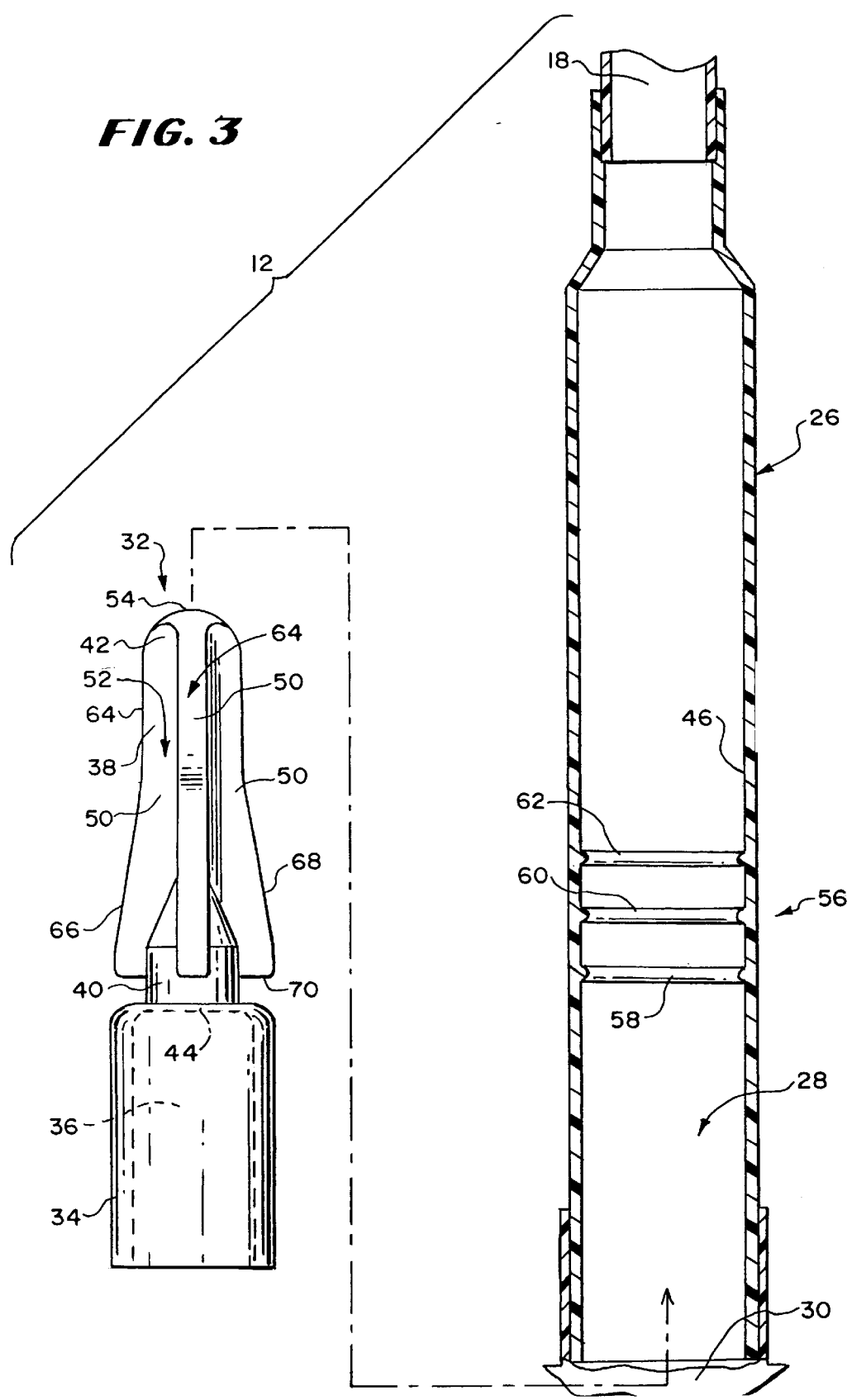
FIG. 3 is an enlarged exploded side view, party in section, of the housing and cannula member that, when assembled, form the breakable cannula assembly shown in FIG. 1.

As FIG. 3 shows, the cannula assembly 12 includes a tubular cannula housing 26, which encloses an interior bore 28. The housing 26 is preferably made from a resilient, flexible material, such as plasticized polyvinyl chloride.

One end of the cannula housing 26 is sealed within a port 30 serving the first bag 14, e.g., by radio frequency heat sealing. The free end of the housing 26 is secured to the transfer tube 18, e.g., by solvent or adhesive. The free end of the housing 26 has a reduced diameter to receive the transfer tube 18 in a tight slip fit.

Figure 2:
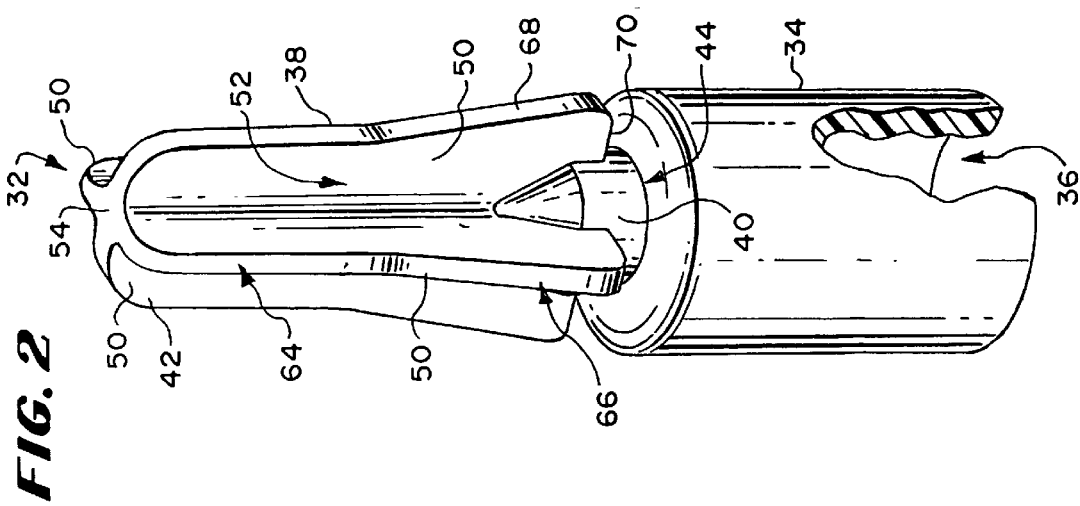
FIG. 2 is an enlarged perspective view, partly broken away and in section, of a cannula member, which forms a part of the breakable cannula assembly shown in FIG. 1.

The cannula assembly 12 also includes a breakable cannula member 32, which FIG. 2 also shows. The cannula member 32 is fixed in position within the cannula housing 26 between the port 30 and the transfer tube 18 (see FIG. 4). The cannula member 32 is preferably made of a rigid plastic material, such as polycarbonate.

As FIGS. 2 to 4 show, the cannula member 32 includes a base 34. The cannula base 34 has an interior lumen 36. The lumen 36 communicates with the port 30.

The cannula member 32 also includes a tip 38. The cannula tip 38 has a back end 40 joined to the base 34. The juncture 44 of the back tip end 40 and the base 34 closes the lumen 36, to normally block passage of fluid between the port 30 and the transfer tube 18.

The cannula tip 38 also includes blunt front end 42, which projects from the base 34 toward the transfer tube 18. As FIG. 4 shows, no part of the blunt front end 42 projects radially outward enough to contact or interfere with the interior wall 46 of the housing bore 28.

A relatively thin region of material (e.g., 0.20 mm in wall thickness) peripherally surrounds the juncture 44 of the back tip end 40 and the base 34. Preferably, the base 34 is contoured near the juncture 44 (see FIGS. 2 and 3), so that the wall thickness of material diminishes gradually in the direction of the juncture 44. This forms a localized region of weakness at the juncture 44, about which the back tip end 40 can be broken free from the base 34.

More particularly, the user can deflect the tip 38 relative to the base 34 inside the resilient, flexible housing 26 (as shown in FIGS. 5 and 6 and by arrows 74 and 78 in FIG. 4). This manual manipulation breaks the back tip end 40 from base 34 about the juncture 44. When the cannula tip 38 is broken free of the base 34 (see FIG. 5), the periphery of the juncture 44 defines an open passage 48. The passage 48 opens communication between the port 30 and the transfer tube 18 through the base lumen 36 and housing bore 28.

The parting of the back tip end 40 from the base 34 is made easier and more reliable by forming the cannula member from a rigid plastic material, such as polycarbonate. Polycarbonate is a preferred material because its hardness and dimensions remain unchanged during heat sterilization.

The use of a polycarbonate material also lends strengths to the juncture 44. The polycarbonate material provides mechanical strength in the juncture 44 sufficient to resist unintended movement of the cannula tip 38 relative to base 34 during normal handling, including centrifugation. Still, the polycarbonate material in the juncture 44 yields in a consistent fashion in response to a focused bending force. The polycarbonate material also breaks cleanly about the juncture 44 to leave a clear, open annular passage 48.

As best shown in FIG. 2, the cannula tip 38 also includes at least two radially spaced vanes 50, which extend along the axis of the tip 38. The illustrated embodiment shows four vanes 50, which are equally radially spaced about the periphery of the tip 38. The spaces between the vanes 50 form channels 52 through which fluid can flow.

The vanes 50 of the cannula tip 38 are collectively tapered along the axis of the tip 38, to provide different maximum outside diameters. The front or leading portion 64 of the vanes 50 is located about the front tip end 42. The diameter of the leading portion 64 is less than the reduced interior diameter of the ribbed area 56, thereby being free of interference or frictional engagement with the interior wall 46 of the bore 28. The potential of puncture or damage to the housing wall 46 by the leading portion 64 during handling or centrifugation is thereby minimized.

Furthermore, the vanes 50 are mutually rounded at the terminus of the front tip end 42, to form a smooth, blunt surface 54. This smooth, blunt surface 54 will not puncture or otherwise apply concentrated point contact force against the interior wall 46 of the housing 26, should the housing 26 bend into contact with the cannula tip 38 during handling or centrifugation.

The vanes 50 also include a back or trailing portion 66. Here, the vanes 50 collectively flare or taper outward, forming a ramped surface 68 of increasing diameter toward the back tip end 40. The surface 68 ramps the trailing portion 66 to a maximum second diameter. The maximum second diameter is generally the same as or less than the interior diameter of the bore 28 outside the ribbed area 56. Therefore, the trailing portion 66 is also free of interference or frictional engagement with the interior wall 46 of the bore 28. As with the leading portion 64, the potential of puncture or damage to the housing wall 46 by the trailing portion 66 during handling or centrifugation is thereby minimized.

The trailing portion 66 terminates short of the back tip end 40 with a step surface 70. The plane of the step surface 70 abruptly reduces the maximum second diameter back to the first diameter, or less, for the remainder of the back tip end 40.

After being broken free of the base 34, the cannula tip 38 should be moved away from the base passage 48, to assure that fluid flow through the passages 48 is not obstructed. It is important to stabilize the freed cannula tip 38 within the housing 26 against unwanted displacement either toward the base passage 48 or toward the transfer tube 18. This displacement can occur, e.g., due to fluid flow about the cannula tip 38, or due to shaking or gravity forces during normal handling. Unintended displacement of the freed cannula tip 38 can result in an obstruction to fluid flow through the housing 26.

For this purpose, the cannula housing 26 includes a ribbed area 56 between the cannula passage 48 and the transfer tube 18. In the illustrated embodiment (see FIGS. 3 and 4), the ribbed area 56 comprises a number of axially spaced, annular rings 58, 60, and 62. The rings 58, 60, and 62 project a set distance outward from the wall 46 into the bore 28 of the housing 26. The ribbed area 56 constitutes a localized region where the interior diameter of the housing bore 28 is reduced. In particular, the reduced interior diameter of the ribbed area 56 interferes with the maximum second diameter of the trailing portion 66, but it does not interfere with the first diameter of the leading portion 64.

As FIG. 4 shows, when the cannula member 32 is in its normal, unbroken condition, the ribbed region 56 extends generally along the mid-portion of the cannula tip 38, between the front end 42 and back end 40. Here, the outside diameter of the cannula tip 38 is less than the reduced interior diameter of the ribbed region 56. Accordingly, there is no interference between the ribbed region 56 and the cannula tip 38.

As FIG. 5 shows, bending the housing 26 in a selected first direction across its axis 76 (arrow 74 in FIG. 5) (e.g., to the right in FIG. 5) deflects the cannula tip 38 relative to the cannula base 34. The deflection breaks the juncture 44 to form the passage 48. The deflection also advances the ramp surfaces 68 of the vanes 50 opposite to the direction of the deflection (i.e., on the left side of the tip 38 in FIG. 5) into interference with the first ring 58. The left side ramp surfaces 68 will apply radial pressure against the ring 58. Due to the resilient, flexible nature of the material of the housing 26, the first-encountered ring 58 will radially expand or yield, to accommodate passage of the left side ramp surfaces 68 past it. Eventually, the ring 58 encounters the left side step surfaces 70. The resilient, flexible nature of the housing material will return the ring 58 back to its normal restricted dimension. The first-encountered ring 58 will then project into the housing bore 28 behind the left side step surfaces 70.

As FIG. 6 shows, bending the housing 26 in a second direction across its axis 76 (arrow 78 in FIG. 6) (e.g., to the left in FIG. 6) rocks or deflects the cannula tip 38 in a different path relative to the cannula base 34. The left side step surfaces 70 pivot against the first ring 58, as the ramp surfaces 68 opposite to the direction of the deflection (i.e., on the right side of the tip 38 in FIG. 6) advance first into interference with the first ring 58, which resiliently yields to allow passage of the right side step surfaces 70, and next into interference with the second ring 60, which also resiliently yields to allow passage of the right side step surfaces 70 past it. The left side step surfaces 70 pivot against the first ring 58, as the opposite right side ramp surfaces 68 advance past the first and second rings 58 and 60.

As FIG. 7 shows, as the housing 26 is returned toward normal alignment with its axis 76 (i.e., moving back to the right from FIG. 6 to FIG. 7), the right side step surfaces 70 pivot against the second ring 60, as the opposite left side ramp surfaces 68 advance past the second ring 60. As FIG. 7 shows, when the housing 26 returns to normal alignment with the axis 76, all step surfaces 70 rest between the ring 60 and the ring 62.

As FIG. 7 shows, the ring 60 resists back travel of the cannula tip 38 toward the base passage 48. The next adjacent ring 62 also resists forward travel of the cannula tip 38 toward the transfer tube 18. As FIG. 5 shows, the ribbed area 56 stabilizes the position of the cannula tip 26 a suitable distance away from both the base passage 48 and the transfer tube 18, thereby keeping fluid flow through the housing 26 free and not obstructed.

Rocking the cannula tip 38 with the housing 26 twice in different directions across the axis of the housing 28 (FIG. 6 and FIG. 7) has simultaneously resulted in freeing the cannula tip 38 from the base 34, as well as advancing the cannula tip 38 past one or more regions of selective interference with the trailing portion 66, to thereby stabilize the position of the cannula tip 38 between the port 30 and the transfer tube 18.

In the illustrated and preferred embodiment, the presence of the third ring 62 provides security, in case the rocking action applied to gain passage of the cannula tip 38 past the first-encountered ring 58 causes the trailing portion 66 to overshoot the next adjacent ring 60. The presence of the third ring 64 checks the overshot, and thereby prevents the cannula tip 38 from moving too far into the housing 26 toward the transfer tube 18.

It should be appreciated that the relative spacing between the rings along the housing axis 76 determines the number of rings that the step surfaces 70 will advance past in response to the rocking action. For example, by spacing the two rings 58 and 60 farther apart than is shown in FIGS. 4 to 7, the cannula tip 38 can be advanced by rocking action into a secure position between them. In this arrangement, rocking the cannula tip 38 in a first direction away from the housing axis 76 (as FIG. 5 shows) will serve to advance one side of the step surfaces 70 past the first ring 60. Rocking the cannula tip 38 in another direction (as FIG. 6 shows) will also advance the other side of the step surfaces 70 past only the first ring 58, because the next-adjacent ring 60 is spaced farther away from the first ring 58 than is shown in FIGS. 5 and 6. In this arrangement, when the cannula tip 38 is returned to alignment with the housing axis 76 (as FIG. 7 shows), all step surfaces 70 will rest between the ring 58 and the ring 60.

In the illustrated embodiment, the system 10 includes directions 80 for manipulating the cannula assembly 12 to break the juncture 44 and to secure the position of the cannula tip 38 in the manners just described.

In a representative embodiment, the housing 26 measures (after steam sterilization) about 55.1 mm in overall length, of which the end surrounding the cannula member 32 constitutes about 41.7 mm in length. The housing bore 28 surrounding the cannula member 32 has an interior diameter (after steam sterilization) of about 6.4 mm outside of the ribbed area 56 and an interior diameter of about 6.1 mm about each ring 58, 60, and 62.

In a representative embodiment, the cannula member 32 measures about 25.6 mm in overall length, of which the base 28 constitutes about 10.5 mm, and the tip 38 constitutes about 15.1 mm. In this embodiment, the base 28 has an outside diameter of about 6.55 mm, with an inside diameter for the lumen 36 of about 4.86 mm. The juncture 44 of the back tip end 40 and the base 34 measures about 4 mm in diameter.

In a representative embodiment, the leading portion 54 of the vanes 50 has a maximum diameter of about 4 mm, and the trailing portion 66 of the vanes 50 has a maximum diameter of about 6.4 mm (i.e., interfering with the 6.1 mm diameter of the rings 58, 60, and 62, but not interfering with the same 6.4 mm diameter of the bore 28 outside the ribbed area 56).

In a representative embodiment having a housing 26 and a cannula member 32 dimensioned as just described, the first ring 58 is spaced about 20.5 mm from the closest end of the housing 26 (i.e., the end that is secured in the port 30), the second ring 60 is spaced about 22.9 mm from this end, and the third ring 62 is spaced about 25.3 mm from this end. In this arrangement, the spacing between adjacent rings is about 2.4 mm. The spacing can, of course, vary somewhat due to the effects of steam sterilization.

Various features of the invention are set forth in the following claims.

We claim:

1. A breakable seal for a fluid path comprising
   a resilient housing comprising a wall defining a bore having an axis and an interior diameter and including a number of rings, spaced apart along the axis, protruding from the wall into the bore, each ring having a restricted diameter less than the interior diameter of the wall,
   a cannula assembly in the bore comprising a base, a tip, a breakable juncture between the tip and base, the tip including a trailing portion, which carries at least one projection extending from different sides of the tip and constructed to frictionally engage the rings, and
   instructions for manipulating the breakable seal following a method comprising the steps of
      bending the resilient housing in a first direction across the axis to deflect the tip and open the breakable juncture, while also advancing one side of the projection past frictional engagement with a first one of the rings, and
      bending the resilient housing in a second direction across the axis to pivot the one side of the projection against the first ring while an other side of the projection advances past frictional engagement with the first ring.

2. The breakable seal according to claim 1
   wherein the number of rings includes a second ring spaced from the first ring, whereby all sides of the projection are between the first and second rings.

3. A breakable seal for a fluid path comprising
   a resilient housing comprising a wall defining a bore having an axis and an interior diameter and including a number of rings, spaced apart along the axis, protruding from the wall into the bore, each ring having a restricted diameter less than the interior diameter of the wall,
   a cannula assembly in the bore comprising a base, a tip, a breakable juncture between the tip and base, the tip including a trailing portion, which carries at least one projection extending from different sides of the tip and constructed to frictionally engage the rings, and
   instructions for manipulating the breakable seal following a method comprising the steps of
      bending the resilient housing in a first direction across the axis to deflect the tip and open the breakable juncture, while also advancing one side of the projection past frictional engagement with a first one of the rings,
      bending the resilient housing in a second direction across the axis to pivot the one side of the projection against the first ring while an other side of the projection advances past frictional engagement with a second one of the ring, and
      returning the resilient housing to alignment with the axis to pivot the other side of the projection against the second ring while the one side of the projection advances past frictional engagement with the second ring.

4. The breakable seal according to claim 3
   wherein the number of rings includes a third ring spaced from the second ring at a position along the axis opposite to the first ring, whereby all sides of the projection are between the second and third rings.

5. The breakable seal according to claim 1 or 3
   wherein the cannula assembly comprises a non-polyvinyl chloride material.

6. The breakable seal according to claim 5
   wherein the non-polyvinyl chloride material comprises polycarbonate.

7. The breakable seal according to claim 1 or 3
   wherein the tip includes a leading portion free of projections to frictionally engage the wall or the rings.

8. The breakable seal according to claim 7
   wherein the leading portion of the tip terminates with a rounded surface free of projections to frictionally engage the wall or the ribbed region.

9. The breakable seal according to claim 7
   wherein the tip includes a number of radially spaced-apart vanes extending along the tip and together forming the leading portion and the trailing portion.

10. The breakable seal according to claim 9
    wherein the tip includes an axis, and
    wherein the vanes taper radially from the tip along the axis from a first diameter to a second diameter greater than the first diameter.

11. The breakable seal according to claim 1 or 3
    wherein the trailing portion is free of projections making frictional engagement with the wall.

12. A method for manipulating a breakable seal for a fluid path having a resilient housing comprising a wall defining a bore having an axis and an interior diameter and including a number of rings, spaced apart along the axis, protruding from the wall into the bore, each ring having a restricted diameter less than the interior diameter of the wall, and a cannula assembly in the bore comprising a base, a tip, a breakable juncture between the tip and base, the tip including a trailing portion, which carries at least one projection extending from different sides of the tip and constructed to frictionally engage the rings, the method comprising the steps of bending the resilient housing in a first direction across the axis to deflect the tip and open the breakable juncture, while also advancing one side of the projection into frictional engagement with a first one of the rings, and bending the resilient housing in a second direction across the axis to pivot the one side of the projection against the first ring while an other side of the projection advances into frictional engagement with the first ring, whereby all sides of the projection are in frictional engagement with the first ring.

13. A method for manipulating a breakable seal for a fluid path having a resilient housing comprising a wall defining a bore having an axis and an interior diameter and including a number of rings, spaced apart along the axis, protruding from the wall into the bore, each ring having a restricted diameter less than the interior diameter of the wall, and a cannula assembly in the bore comprising a base, a tip, a breakable juncture between the tip and base, the tip including a trailing portion, which carries at least one projection extending from different sides of the tip and constructed to frictionally engage the rings, the method comprising the steps of bending the resilient housing in a first direction across the axis to deflect the tip and open the breakable juncture, while also advancing one side of the projection into frictional engagement with a first one of the rings, bending the resilient housing in a second direction across the axis to pivot the one side of the projection against the first ring while an other side of the projection advances into frictional engagement with a second one of the ring, and returning the resilient housing to alignment with the axis to pivot the other side of the projection against the second ring while the one side of the projection advances into frictional engagement with the second ring, whereby all sides of the projection are in frictional engagement with the second ring.

\* \* \* \* \*